United States Patent [19]

Shah

[11] Patent Number: 5,556,428
[45] Date of Patent: Sep. 17, 1996

[54] APPARATUS AND METHOD FOR PROMOTING GROWTH AND REPAIR OF SOFT TISSUE

[76] Inventor: Mrugesh K. Shah, 4314 Montevideo, Pasadena, Tex. 77504

[21] Appl. No.: 128,809

[22] Filed: Sep. 29, 1993

[51] Int. Cl.⁶ .............................. A61F 2/08; A61B 17/08
[52] U.S. Cl. .................. 623/13; 623/11; 606/151
[58] Field of Search ................... 623/11, 13, 66; 606/86, 151, 152, 153

[56] References Cited

U.S. PATENT DOCUMENTS

| | | | |
|---|---|---|---|
| 2,647,743 | 6/1949 | Cook | 267/1 |
| 3,842,441 | 10/1974 | Kaiser | 623/13 |
| 3,971,670 | 7/1976 | Homsy | 156/196 |
| 3,973,277 | 8/1976 | Semple et al. | 3/1 |
| 3,988,783 | 11/1976 | Treace | 3/1 |
| 4,149,277 | 4/1979 | Bokros | 3/1 |
| 4,187,558 | 2/1980 | Dahlen et al. | 3/1 |
| 4,301,551 | 11/1991 | Dore et al. | 3/1 |
| 4,400,833 | 8/1983 | Kurland | 623/13 |
| 4,455,690 | 6/1984 | Homsy | 3/1 |
| 4,469,101 | 9/1984 | Coleman et al. | 128/334 |
| 4,520,797 | 6/1985 | Peterson | 128/20 |
| 4,597,766 | 7/1986 | Hilal et al. | 623/13 |
| 4,605,414 | 8/1986 | Czajka | 623/13 |
| 4,723,548 | 2/1988 | Lalonde | 128/335 |
| 4,773,910 | 9/1988 | Chen et al. | 623/13 |
| 4,776,851 | 10/1988 | Bruchman | 623/13 |
| 4,778,468 | 10/1988 | Hunt et al. | 623/16 |
| 4,781,191 | 11/1988 | Thompson | 128/334 |
| 4,917,700 | 4/1990 | Aikins | 623/13 |
| 4,950,293 | 8/1990 | Beacon et al. | 623/13 |
| 4,955,910 | 9/1990 | Bolesky | 623/13 |
| 4,979,956 | 12/1990 | Silvestrini | 623/13 |
| 5,108,433 | 4/1992 | May et al. | 623/13 |
| 5,163,948 | 11/1992 | Kummer | 606/152 |
| 5,281,422 | 1/1994 | Badylak et al. | 623/11 |

FOREIGN PATENT DOCUMENTS

| | | | |
|---|---|---|---|
| 0432743 | 6/1991 | European Pat. Off. | 606/151 |
| 0227454 | 9/1943 | Switzerland . | |

*Primary Examiner*—Debra S. Brittingham
*Attorney, Agent, or Firm*—Pravel, Hewitt, Kimball & Krieger

[57] ABSTRACT

Apparatus and method for inducing growth of soft tissues including skin, ligaments, tendons, blood vessels, and spinal cord which includes a tensioned spring causing the application of force on the soft tissue in the direction of the desired growth. The device also includes means for attaching the tensioned spring to the tissue and means for maintaining tension on the spring as the tissue grows.

9 Claims, 3 Drawing Sheets

APPARATUS AND METHOD FOR PROMOTING GROWTH AND REPAIR OF SOFT TISSUE

FIELD OF THE INVENTION

This invention relates to a temporary prosthetic device, more specifically, a surgically implantable device to promote growth of soft tissue, such as muscles, ligaments or tendons, venous tissue, skin tissue, and spinal cord.

DESCRIPTION OF THE RELATED ART

When a ligament or tendon is ruptured or severed, it often must be replaced by other biological materials such as skin or by an artificial prosthesis. Alternatively, repair of a severed ligament or tendon may be accomplished by suturing the severed ends together or, when the tear is at the location of the joint, by attaching the severed tendon or ligament directly to the bone by means of a bone staple or pin.

However, when trauma to the ligament or tendon results in the remaining fragment of tendon or ligament not being of a sufficient length to permit suture or permanent attachment to the bone, alternate methods must be employed to secure the ligament or tendon to the bone.

The prior art is replete with prosthetic devices which seek to permanently replace a missing or damaged tendon or ligament. See, for example, U.S. Pat. Nos. 4,301,551; 3,971,670; 4,149,277; 4,979,956; 4,950,293; 4,776,851; 4,773,910; 4,605,414; 4,597,766; and 3,988,783. See also, U.S. Pat. Nos. 4,778,468; 3,971,670; 4,917,700; 4,187,558; and 4,455,690. Some of these devices are designed to promote growth of new ligament or tendon tissue. However, the growth is generally along and within a template formed by a permanent prosthetic device. Similarly, repair of torn or damaged skin or other tissue, nerves and blood vessels may be achieved by suturing or by replacement with grafted tissues.

Accordingly, it is desirable to provide for a non-permanent, removable mechanism for promoting the growth of soft tissue, in particular ligaments, tendons, blood vessels, nerves, skin and other tissues.

SUMMARY OF THE INVENTION

The present invention is directed to an implantable device for promoting growth of soft tissue, such as severed ligaments and tendons, skin for grafting, venous tissue, nerves and spinal cord tissue. The device is intended to stimulate growth of the tissue in a desired direction. Once the tissue has achieved the desired growth and strength, the device may be removed, and normal reattachment of the tissue accomplished.

More specifically, the present invention includes a tensioning device, one end of the tensioning device being attached to soft tissue, such as muscles, ligaments or tendons, blood vessels, skin, and the like, with the other end of the tensioning device fixed (e.g., to bony tissue), to anchor the tensioning device. When the tensioning device is positioned, force is applied to the soft tissue in a direction which promotes growth of the tissue as desired (e.g., toward a bony tissue anchor). The present invention enables tension to be maintained in the tissue, even when the tissue becomes elongated during growth.

The present invention may be used to repair a break or tear in soft tissue which has no bony attachment site. Each end of the tensioning device may be anchored to a severed end of the soft tissue with applied extension or compression of the tensioning device urging elongation of the severed ends toward one another. Force is maintained on the tissue by the tensioning device so as to cause a gradual stretching of the severed ends of the soft tissue until the ends grow to a sufficient length for subsequent repair.

Once the soft tissue has achieved its desired growth, the tensioning device is removed and the elongated tissue sutured, pegged or stapled in its desired location. Where the present invention is used to repair severed soft tissue members, the device is removed once the ends of the soft tissue members are in contact for repair.

The present invention is also used to induce the growth of soft tissues for removal and use in grafting procedures. Healthy tissue is induced to grow beyond its normal size, and this excess growth is excised and transplanted to another site in a patient. This method provides a source of uniquely compatible tissue for grafting the patient's own tissue, without significantly disturbing the functioning of tissue from which the graft is drawn.

BRIEF DESCRIPTION OF THE DRAWINGS

A better understanding of the invention can be obtained when the following detailed description of exemplary embodiments is considered in conjunction with the following drawings, in which.

DETAILED DESCRIPTION OF THE PREFERRED EMBODIMENT

The present invention is intended to promote the growth of soft tissue by applying a force to the soft tissue in the desired direction of growth.

As shown in FIGS. 1–6, the tensioning device of the present invention generally includes a spring means 10 adapted to provide tension or force to soft tissue 4 in order to cause growth in the desired direction a, and an attachment means 2 for attaching the soft tissue to the spring, permitting tension to be applied.

The spring 10 may be a helical or spiral spring, a constant force spring, and the like, which are adapted to provide tension on soft tissue to promote its growth. The attachment means 2 may be surgical hooks, sutures, staples, and the like, for attaching the soft tissue to the device and permitting force to be transferred thereto. The invention may be further understood by reference to the following description of the preferred embodiments.

Figure 1:
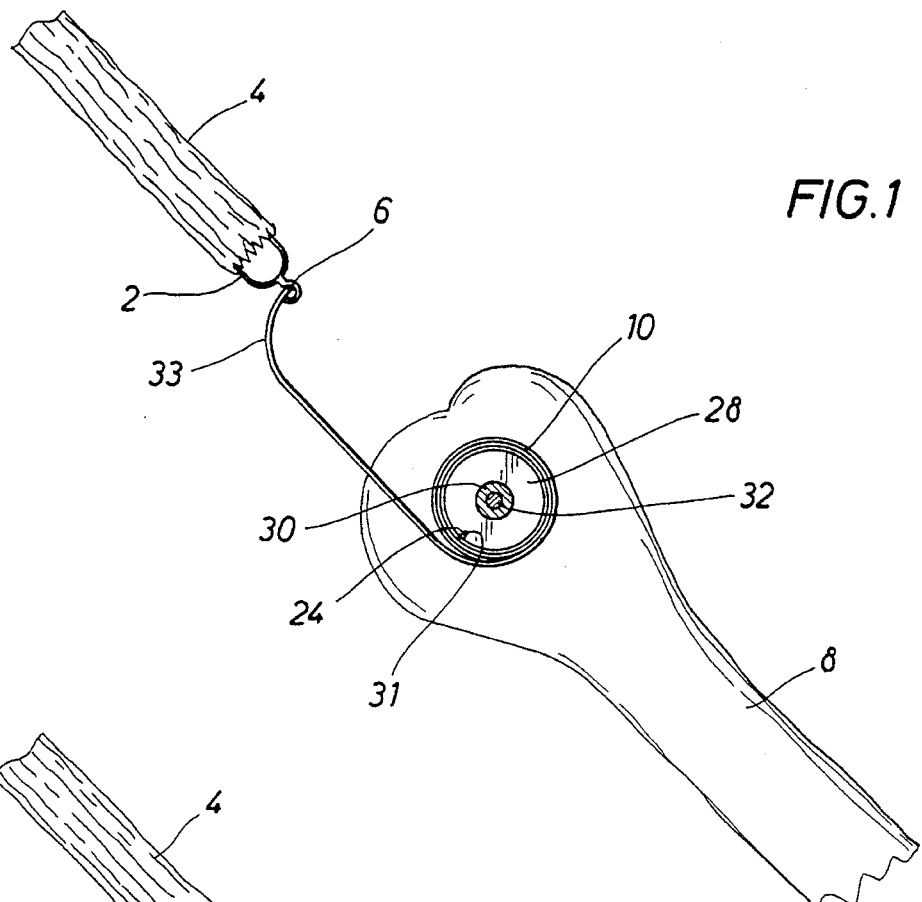
FIG. 1 is a representation of one embodiment of the present invention connecting soft tissue to bony tissue utilizing a force spring to reunite tissue and bone.

FIG. 1 is a representation of a preferred embodiment of the present invention where the growth of severed or torn soft tissue, such as tendons, ligaments or muscle, is promoted in a desired direction a, toward the normal site of insertion of the soft tissue on bony surfaces or other anchoring structures. In the preferred embodiment of FIG. 1, the tensioning device is composed of a constant force spring 10 mounted on a bushing 28, which is adapted to rotate freely on shaft 30. The inner end of the spring 31 is bent over to engage a slit 24 in the bushing. The embodiment of FIG. 1 further includes a plurality of surgical hooks 2 attached to the outer end 33 of the spring 26 adjacent to the severed soft tissue 4. The hooks 2 are surgically inserted into the soft tissue 4 to provide an attachment means for the spring 10. It will be appreciated that means other than hooks 2, such as staples, sutures, collars, clamps or clips may be used to attach one end of the spring 10 to the severed soft tissue 4.

The tensioning device is anchored to the bone 8 by a fixation means 32, e.g., surgical pin, tap or screw, that passes through the shaft 30 on the bushing 28 via a hole in the shaft 30, and into the bone 8. In the preferred embodiment all of the components of the tensioning device are formed of biocompatible materials. It will be appreciated that by anchoring the tensioning device at the bone 8 and attaching the outer free end 33 of the spring 10 to the severed tissue 4 through the hook means 2, the force of the spring 10 creates a tension in the soft tissue 4 in the direction a of the bone 8. The force exerted by the spring 10 urges the soft tissue 4 to stretch or grow in the direction a of the force. As the soft tissue 4 grows toward the bone 8, the spring 10 coils upon itself, decreasing the distance between the soft tissue 4 and the bone 8. Once sufficient growth has occurred, such that the soft tissue 4 and the bone 8 are in close proximity, the tensioning device is removed. The soft tissue 4 is then surgically stapled, sutured or otherwise attached to the bone 8.

In a preferred embodiment, a constant force spring formed of pre-stressed, flat spring stock which coils up on itself when free is used. Unlike spring types whose force decreases with decreasing deflection, constant force springs exert a constant force irrespective of the length of its deflection. Stated another way, the force exerted by a constant force spring is generally unvarying, and does not depend on the extent to which the spring is wound or unwound. Thus, with growth of the attached tissue, no slack in either the soft tissue 4 or spring 10 occurs and growth sufficient to place the severed tissue 4 and bone 8 in close proximity may be accomplished.

It may, however, be desirable under certain applications to either increase, decrease or vary the force exerted by the spring 10 as a function of position of the severed tissue 4 relative to the bone 8. For example, it may be desirable to decrease the force exerted by the tensioning device as the severed tissue grows so as not to tear or sever the newly grown tissue. Thus, a spring exhibiting a negative force gradient would be desired. All of these spring types, which may exert constant, variable, negative and positive gradients are contemplated and have been exemplified in U.S. Pat. No. 2,647,743.

Figure 2:
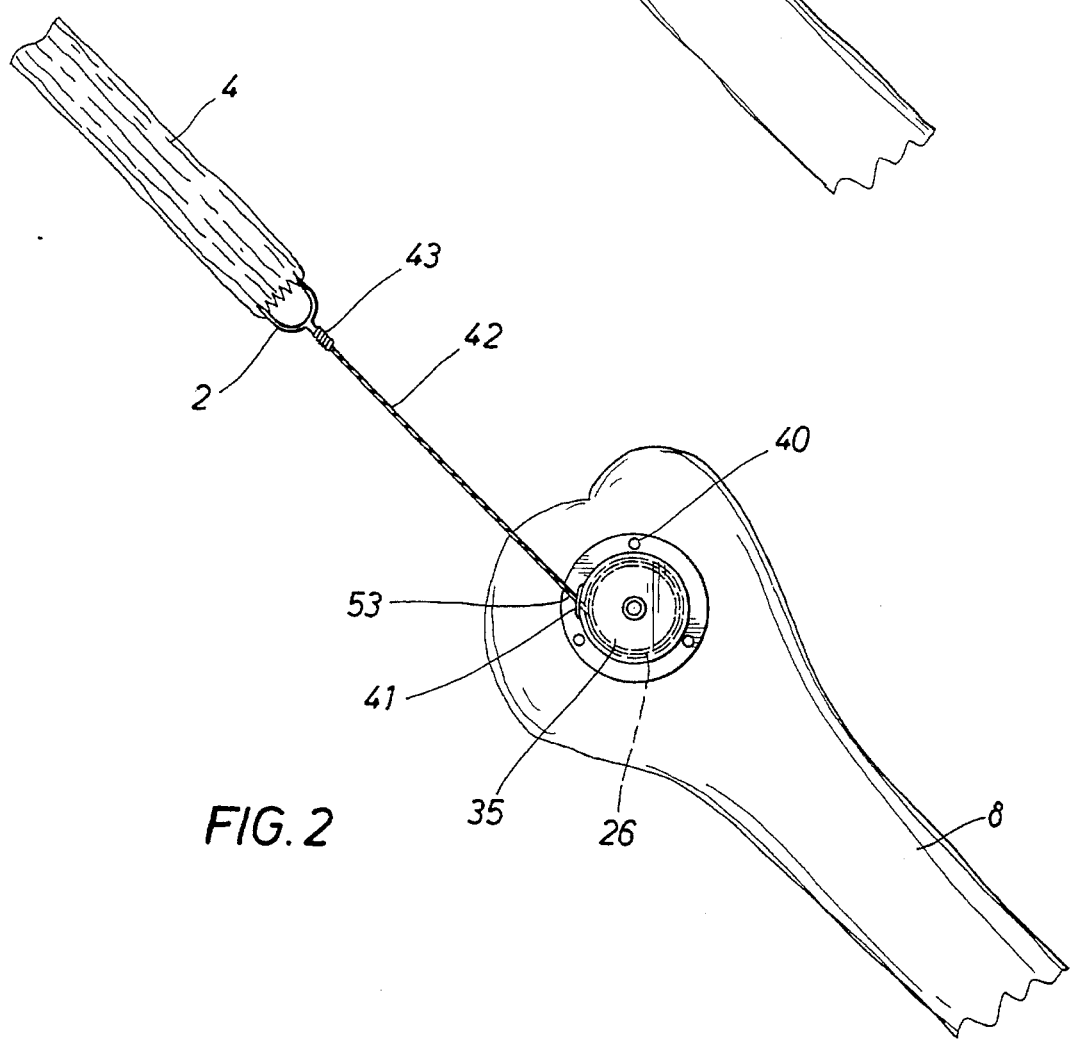
FIG. 2 is a representation of one embodiment of the present invention connecting soft tissue to bony tissue, utilizing a spring powered reel to reunite tissue and bone.

In an alternative preferred embodiment, as shown in FIG. 2, the previously described tensioning device is enclosed in a biocompatible housing 35 that is attached to bone 8 by screws, nails, pins or taps which are be inserted in the bone 8 through holes in the housing 35. In this embodiment, the spring 10, the shaft 30, and the bushing 28 are contained within the housing 35 and, thus, need not be made of biocompatible material. This embodiment functions in a manner similar to the embodiment shown in FIG. 1, except that the force of the spring 10 is mediated through a biocompatible cable 42 attached at one end 43 to the outer end of the spring 33 and terminating in a hook means 2 at the other end 53 of the cable 42. This spring powered reel mediates a constant force upon the soft tissue 4 via the cable 42. As with the constant force spring embodiment of FIG. 1, the constant force applied to the soft tissue in the direction of the bone 8 urges growth of the tissue 4 in the direction of the bone 8. As the tissue 4 grows, the cable 42 retracts into the housing 35, ultimately urging tissue growth to a point where the soft tissue 4 may be inserted in the bone 8 in an appropriate location by staples, sutures or other suitable attachment means.

Figure 3:
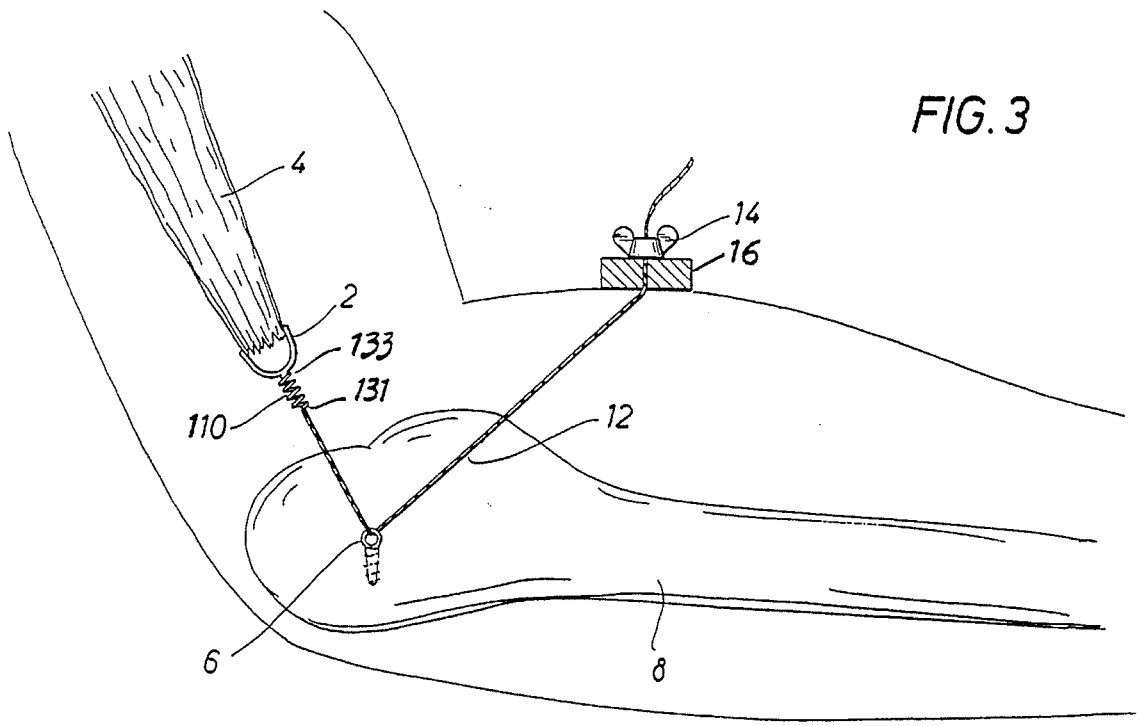
FIG. 3 is a representation of one embodiment of the present invention connecting soft tissue to bony tissue, utilizing a helically-coiled spring in conjunction with a remote adjusting device to reunite tissue and bone.

In the preferred embodiment shown in FIG. 3, the tensioning device is comprised of a helical spring 110 manufactured from a suitable biocompatible material. However, it will be appreciated that other suitable tensioning means, such as a leaf spring, elastic cord or band or other suitable implantable device capable of being placed in tension may be utilized within the present invention. The tensioning device shown in FIG. 3 further includes a plurality of surgical hooks 2 attached to the end of the spring 110 adjacent to the severed soft tissue 4. The hooks 2 are surgically inserted into the soft tissue 4 to provide attachment means for the spring 110. As described above, it will be appreciated that means other than hooks 2, such as staples, sutures and the like may be used to attach one end 133 of the spring 110 to the severed soft tissue 4.

The opposite end 131 of the spring 110 is in communication with a surgical pin or screw 6 fixed, for example, by insertion in a bone 8. It will be appreciated that other suitable means, such as surgical nails or staples may be used to anchor the tensioning device to bone 8. One end of spring 110 is extended to and secured about pin 6 to place the spring 110 and, thereby, severed tissue 4 in tension. The tensioned spring 110 thus promotes the growth of the severed tissue 4 toward pin 6.

As the severed tissue 4 grows toward pin 6, it will be appreciated that the tension in spring 110 will generally decrease, as will the tension applied to the severed tissue 4. Accordingly, the preferred embodiment provides for a means for maintaining tension in the tensioning device as the severed tissue grows. An adjusting means is attached to the tensioning device internal to the patient's body and exits external to the patient's body. Torque is applied to the adjusting means, which in turn, deforms the tensioning device, thus increasing the tension within the tensioning device. In the embodiment of FIG. 3 a surgical tensioning cord or tow 12 is attached to one end 131 of the spring 110, wherein surgical pin 6 operates as a pivot point between helical spring 110 and tow 12. The tow 12 passes through the surrounding soft tissue and exits the body (e.g., through a mounting block 16, including a screw 14). The tow 12 is attached to the shaft of screw 14, which may be rotated and retained within block 16, to place tow 12 in tension which, in turn, stretches the end 131 of spring 110 to maintain tension as the severed tissue 4 grows toward pin 6 and bone 8. It will be appreciated that other adjusting means, such as a metal rod may be used to deform the tensioning device. Further, the present invention contemplates other means for applying tension to and retaining the connecting means, such as an external clip or retaining screw.

Once the severed tissue 4 is in close proximity to bone 8, the tensioning device, including spring 110, hooks 2, pin 6 and tow 12 are removed. The severed tissue 4 is then surgically stapled, sutured or otherwise attached to the bone 8.

Figure 4A:
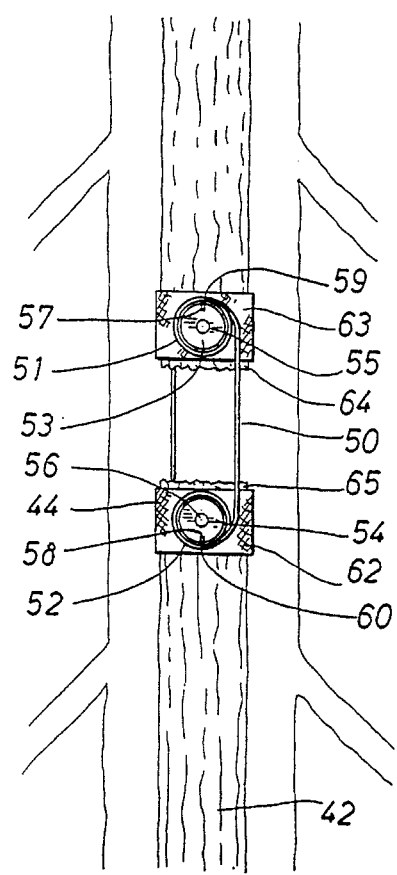
FIG. 4A is a representation of one embodiment of the present invention attached at two opposable points of severed soft tissue urging connection of opposite ends of severed soft tissue.

In another preferred embodiment, the present invention is used to promote growth of the ends of severed tissue toward one another. As shown in FIG. 4A, a constant force spring 50 is coiled at opposed ends to form coils 51, 52, which are mounted on bushings 53, 54 respectively, and which are adapted to rotate freely on shafts 55 and 56 respectively. The inner ends 31 of the constant force springs 57, 58 are bent over to engage slits 59, 60, respectively, in the bushings 53, 54 respectively. The embodiment shown in FIG. 4A further includes sleeves 62, 63, that are attached to the tensioning device through shafts 56, 55 respectively. Each sleeve is placed in contact with one end of the severed tissue, and secured thereto, e.g. by sutures. In FIG. 4A, sleeve 63 is placed securely around one end of the severed spinal cord 64, above the break in the tissue, and sleeve 62 is placed securely around severed end 65, just below the break in the tissue such that sleeves 62, 63 will not move relative to the severed ends 64, 65 of the spinal cord. The sleeves 62, 63 may be made from a variety of materials, the preferred embodiment contemplates the use of fabric sleeves. Other means of attaching the tensioning means to the severed tissue are contemplated, such as collars, pins, sutures, clips and clamps, any means that will hold the position of the shafts 55, 56 relative to the severed tissue 42.

Figure 4B:
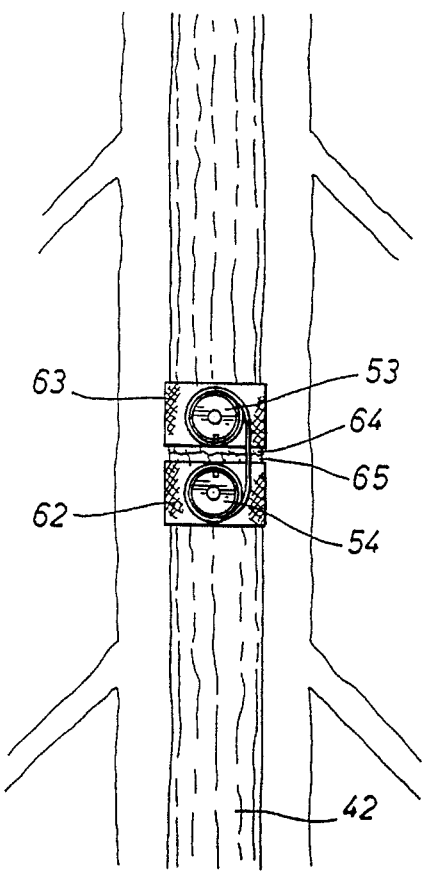
FIG. 4B is a representation of the preferred embodiment shown in FIG. 4A wherein said soft tissue opposable ends have made connection by growing toward one another.

When the tensioning device of the present invention is positioned, as shown in FIG. 4A, coils 51, 52 of each constant force spring 50 will attempt to wind up in the direction of the opposite coil, due to the inherent properties of the constant force spring. The force inherent in the windings creates a tension in each of the severed ends 64, 65 of the spinal cord 42 in the direction b toward the break in the spinal cord. This tension urges the severed ends 64, 65 of the spinal cord to grow toward each other. As the tissue grows, the coils 51, 52 of the constant force springs 50 take up the slack by winding toward each other. The properties of the constant force springs are such that the force generated by the springs is independent of the degree of coiling, thus the tension on the severed ends 64, 65 remains constant during growth. With continued tension, the spinal cord 42 will grow and elongate as indicated in FIG. 4B, thereby bringing both ends 64, 65 of the severed spinal cord into proximity with one another such that these ends 64, 65 may be reunited surgically using staples, sutures or any device that will foster reattachment of the ends.

It will be appreciated that a plurality of constant force springs may be used in the embodiment, and the preferred embodiment contemplates the use of two constant force spring devices mounted on the severed tissue opposed from each other, e.g. at approximately 180°. Preferably, the two spring devices are mounted in opposite orientation such that one appears as the mirror image of the other. The two devices mounted on opposite sides of the severed tissue in opposing orientation promote stability of the device and aid in healing the tissue.

Figure 5:
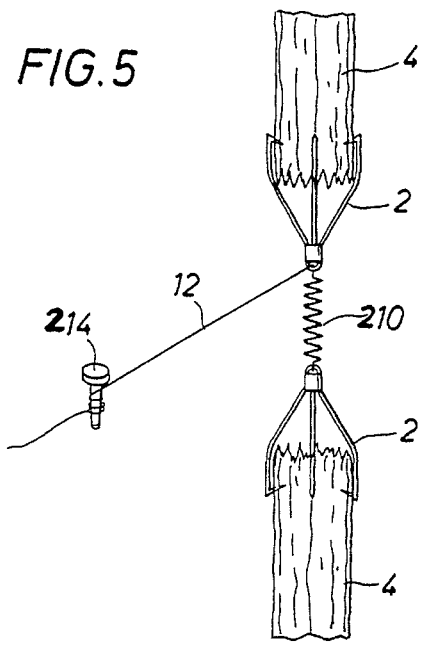
FIG. 5 is a representation of one embodiment of the present invention for connecting opposite ends of severed soft tissue utilizing a helically coiled spring and a remote tensioning device.

In an alternative preferred embodiment as shown in FIG. 5, a helically-coiled spring 210, having plurality of surgical hooks 2 attached to each end of the spring 210 is used to promote grown of two ends of severed tissue towards each other. Surgical hooks 2 on each end of the coiled spring 210 are surgically inserted into the ends of the severed tissue members 4, thereby placing the spring 210 in tension and promoting growth of the severed tissue members 4 toward each other. A surgical cord or tow 12 is attached to the spring 210 to maintain tension. One end of the tow 12 is connected to screw 214, which may be rotated to place tow 12 in tension. As tow 12 is placed in tension, the spring 210 increases tension on the severed tissue members 4 and promotes further growth. It will be appreciated that as the severed tissue members 4 grow, the tensioning device, including spring 210, hooks 2, and screw 214 may be removed and the ends of the severed tissue members 4 connected by means of surgical staple, nail, suture or other suitable means.

Figure 6A:
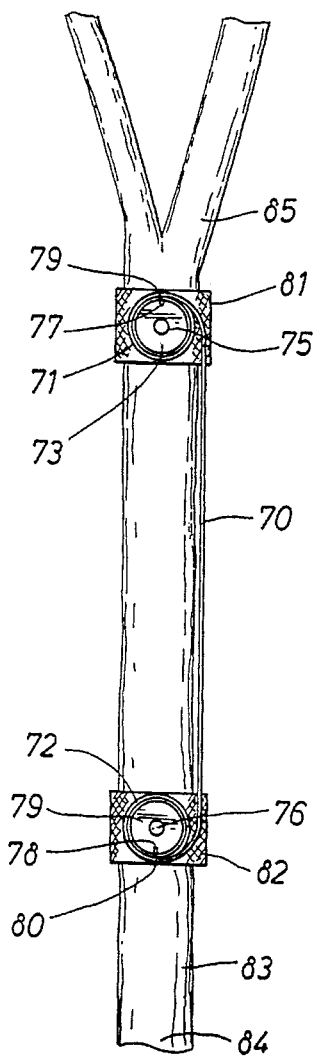
FIG. 6A is a representation of one embodiment of the present invention attached at two points to an intact blood vessel to induce elongation.

In an alternative preferred embodiment, the present invention may be utilized to promote growth of excess normal tissue which may be excised and used in tissue replacement or grafting procedures. In FIG. 6A the tensioning device is comprised of a constant force spring 70 coiled at opposite ends forming coils 71, 72, which are mounted on bushings 73, 74 respectively, which are adapted to fully rotate on shafts 75, 76 respectively. The ends 77, 78 of the constant force spring are bent over to engage slits 79, 80, respectively, in bushings 73, 74 respectively. The embodiment of FIG. 6A further includes sleeves 81, 82 which are attached to the tensioning device through shafts 75, 76 respectively. The sleeves 81, 82 are placed in contact with the blood vessel 83, one sleeve 82 in contact with the distal end 84 of the blood vessel, and another sleeve 81 in contact with the proximal end 85 of the blood vessel. The sleeves 81, 82 are placed relative to each other at a distance sufficient to provide growth of a graft section adequate for excision and transplantation. The sleeves 81, 82 are secured to the blood vessel 83, e.g. by sutures or the like, such that the sleeves 81, 82 will not move relative to the initial position on the blood vessel 83; that is, the sleeves are secured so that they will not slip. Other means of attaching the tensioning means to the soft tissue are contemplated, such as collars, pins, hooks, sutures, clips and clamps.

Figure 6B:
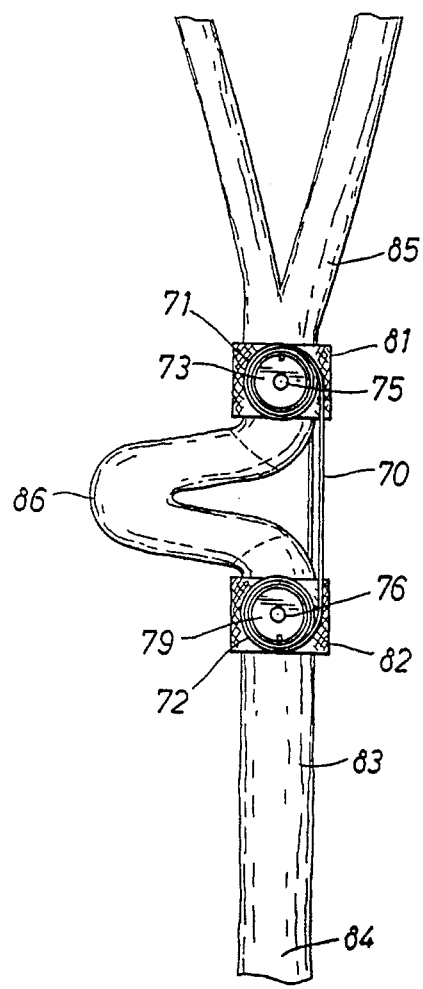
FIG. 6B is a representation of the preferred embodiment shown in FIG. 6A, wherein said blood vessel has been elongated.

When the tensioning device of the present invention is positioned, as shown in FIG. 6A, each coil 71, 72 of the constant force spring 70 will attempt to wind up in the direction of the opposing coil due to the inherent properties of the constant force spring 70. The force inherent in the winding creates a tension in the blood vessel 83 between the proximal end 85 and the distal end 84. The tension urges the proximal end 85 and the distal end 84 to grow toward each other. As the tissue grows, the coils 71, 72 of the constant force spring 70 take up the slack by winding toward each other. The properties of the constant force spring are such that the force generated by the spring is independent of the degree of coiling, thus, the tension on the proximal end 85 and distal end 84 of the blood vessel remains constant during growth. With continued tension, the blood vessel will grow and elongate as indicated in FIG. 6B, thereby providing excess blood vessel tissue 86 which may be excised and used for grafting or transplant purposes. Upon excision of the graft, the normal blood vessel may be repaired such that a graft may be removed without impairing the use of the blood vessel from which it was derived.

It will be appreciated that a plurality of constant force springs may be used in the embodiment and the preferred embodiment contemplates the use of two constant force springs attached to the sleeve and mounted on the severed tissue about 180° opposed from each other. Additionally, the two spring devices are mounted in opposite orientation such that one appears as the mirror image of the other. The use of two springs mounted on opposite sides of the blood vessel in opposite orientation promotes stability of the device and aids in growth of the tissue.

It is presumed that alternative means for attaching the tensioning device to specific tissues are known by those with skill in the art. In addition, alternative means for maintaining tension between the pair of attachment means of the device may also be employed. Such changes are contemplated within the scope of the present invention.

Having described the invention above, various modifications of the techniques, procedures, material and equipment will be apparent to those in the art. It is intended that all such variations within the scope and spirit of the appended claims be embraced thereby.

What is claimed is:

1. A removable biocompatible device for promoting growth of soft tissue comprising:

spring means having a first end and a second end:

attachment means for removably securing said first end of said spring means to a soft tissue;

fixation means for removably securing said second end of said spring means to a second point, such that tension is created by the spring means in the soft tissue, and in a direction along a line drawn from the attachment means to the second point, wherein:

the spring means include at least one pair of opposed coils, and said pair of opposed coils winds up in response to growth of attached soft tissue.

2. The device of claim 1, wherein the spring means is a fixed coil sprang.

3. The device of claim 2, wherein the fixed coil spring exerts a constant force.

4. The device of claim 2, further comprising:

adjustment means for adjusting the tension in the spring.

5. A method for inducing growth of soft tissue comprising:

attaching the device of claim 1 to soft tissue such that tension applied to the soft tissue by the spring means results in elongation of the soft tissue in a direction along a line drawn between the attachment means and the fixation means.

6. A method for preparing graft tissue comprising:

elongating soft tissue by the method of claim 5; and excising elongated tissue for use on grafting tissue.

7. The device of claim 1, wherein the attachment means is from the group consisting of surgical hooks, staples, sutures, collars, clamps and clips.

8. The device of claim 1, wherein the spring means automatically maintains tension on the soft tissue as the attached soft tissue grows.

9. The device of claim 1, wherein the spring means automatically maintains constant force on the soft tissue as the attached soft tissue grows.

* * * * *